United States Patent
Decker

(10) Patent No.: US 10,937,639 B2
(45) Date of Patent: Mar. 2, 2021

(54) PRECURSOR SELECTION FOR DATA-DEPENDENT TANDEM MASS SPECTROMETRY

(71) Applicant: Bruker Daltonik GmbH, Bremen (DE)

(72) Inventor: Jens Decker, Bremen (DE)

(*) Notice: Subject to any disclaimer, the term of this patent is extended or adjusted under 35 U.S.C. 154(b) by 0 days.

(21) Appl. No.: 16/429,576

(22) Filed: Jun. 3, 2019

(65) Prior Publication Data
US 2019/0371585 A1 Dec. 5, 2019

Related U.S. Application Data

(60) Provisional application No. 62/680,355, filed on Jun. 4, 2018.

(51) Int. Cl.
*H01J 49/00* (2006.01)
*H01J 49/40* (2006.01)

(52) U.S. Cl.
CPC ........ *H01J 49/0036* (2013.01); *H01J 49/004* (2013.01); *H01J 49/40* (2013.01)

(58) Field of Classification Search
CPC .... H01J 49/00; H01J 49/0036; H01J 49/0045; H01J 49/02
USPC ................................. 250/281, 282
See application file for complete search history.

(56) References Cited

U.S. PATENT DOCUMENTS

| | | |
|---|---|---|
| 2004/0245452 A1 | 12/2004 | Bateman et al. |
| 2006/0060768 A1* | 3/2006 | Kaufman ............ H01J 49/42 250/281 |
| 2010/0032561 A1* | 2/2010 | Giles ............... H01J 49/4235 250/283 |
| 2010/0286927 A1 | 11/2010 | Horn et al. |
| 2015/0041636 A1 | 2/2015 | Giles et al. |
| 2016/0268114 A1 | 9/2016 | Giles et al. |
| 2016/0274058 A1 | 9/2016 | Wildgoose |
| 2017/0178887 A1 | 6/2017 | Park et al. |
| 2019/0154632 A1 | 5/2019 | Harder et al. |

FOREIGN PATENT DOCUMENTS

| | | |
|---|---|---|
| DE | 10361023.5 A1 | 1/2005 |
| DE | 102017111067.4 A1 | 6/2016 |
| EP | 3165914 A | 5/2017 |
| GB | 2514455 A | 11/2014 |
| GB | 2555187 A | 4/2018 |
| WO | 2005001869 A2 | 1/2005 |
| WO | 2013140132 A2 | 9/2013 |
| WO | 2016067204 A1 | 5/2016 |

* cited by examiner

*Primary Examiner* — Jason L McCormack
(74) *Attorney, Agent, or Firm* — Benoit & Côté Inc.

(57) ABSTRACT

The invention relates to selection of precursors from a measured mobility-mass map for tandem mass spectrometry and is based on processing a peak list from measured signals and clustering these peaks in the mobility-mass space.

22 Claims, 4 Drawing Sheets

PRECURSOR SELECTION FOR DATA-DEPENDENT TANDEM MASS SPECTROMETRY

BACKGROUND OF THE INVENTION

Field of the Invention

The invention relates to methods for data-dependent tandem mass spectrometry, in particular to precursor selection as part of the acquisition of fragment mass spectra for complex substance mixtures, like digest peptides in a bottom-up proteomics workflow.

Description of the Related Art

Bottom-up proteomics is a method to identify proteins and characterize their amino acid sequences and post-translational modifications by proteolytic digestion of proteins extracted from a biological sample prior to analysis by mass spectrometry, in particular by tandem mass spectrometry. There is an increasing interest in the identification of as many peptides and proteins as possible. Hybrid mass spectrometric systems which couple mass spectrometry with ion mobility spectrometry have been shown to improve measurements to reach this goal.

As an example of performing a bottom-up proteomics workflow, a mass spectrometric system can be used which combines an up-front substance separator, e.g., a liquid chromatograph (LC), a mobility separator, a mass filter (usually an RF quadrupole mass filter), a fragmentation cell and a downstream time-of-flight mass analyzer with orthogonal ion injection. An ion trap may be used to accumulate ions upstream of the ion mobility separator, and a drift tube ion mobility separator to separate the ions in time according to mobility.

In a first measurement cycle, a mobility-mass map can be measured, using the mobility separator and the time-of-flight analyzer without filtering masses and fragmenting ions. In a second measurement cycle, ions from the ion accumulator are again separated in time according to mobility. The mass filter is adjusted to select predetermined ion species of interest (precursor ions) during the specific drift time of the ion species, which are then fragmented in the fragmentation cell, and the desired fragment ion spectrum is acquired by the time-of-flight mass analyzer. U.S. Pat. No. 6,960,761 B2 ("INSTRUMENT FOR SEPARATING IONS IN TIME AS FUNCTIONS OF PRESELECTED ION MOBILITY AND ION MASS") discloses this data-dependent acquisition of fragment mass spectra using a hybrid system with a drift type mobility separator and time-of-flight mass analyzer with orthogonal ion injection.

The recently introduced Parallel-Accumulation SErial-Fragmentation (PASEF) acquisition mode uses a hybrid mass spectrometric system with a trapping ion mobility separator and a time-of-flight mass analyzer with orthogonal ion injection (TIMS-OTOF) and separates ions in time according to mobility and elutes ion-packages from the TIMS device (Meier et al., J. Proteome Res., 2015, 14 (12), pp 5378-5387). Precursors are detected either in the mass or mobility dimension. The quadrupole isolates distinct precursor species during the few milliseconds they actually elute from the TIMS device and immediately switches to the next precursor resulting in improved speed and sensitivity compared to traditional tandem MS scan modes.

In view of the foregoing, there is still a need for a fast and reliable method to select relevant and non-redundant precursor ions for a tandem MS analysis from combined mobility-mass spectra, in particular if the combined spectra comprise signals of a plurality of different ion species under the time constraints dictated by the chromatographic retention time length.

SUMMARY OF THE INVENTION

The invention provides a method for acquiring fragment mass spectra of substances from complex substance mixtures by a mass spectrometric system comprising an ion source, a mobility separator, a mass filter, a fragmentation cell, and a mass analyzer, comprising the steps of a first and a second measurement cycle.

The first measurement cycle comprises the steps of: (a) separating a first set of ions in time according to mobility using the mobility separator and subsequently further separating the ions according to mass using the mass analyzer and measuring signals of the separated ions; (b) processing a peak list from the signals, wherein a mobility scan time, a mass and an intensity is assigned to each peak of the peak list; (c) assigning weights to the peaks wherein a higher weight is assigned to a peak when other peaks are near to that peak and, in particular, when other peaks of high intensity are near to that peak; and (d) selecting peaks which have weights above a predetermined threshold and/or have the highest weighted intensities within a certain neighborhood and whose mobility scan times are separated from each other by a minimum duration.

The second measurement cycle comprises the steps of: (e) separating a second set of ions in time according to mobility using the mobility separator and subsequently filtering ion species according to mass using the mass filter, wherein the mobility scan times and the masses of the filtered ion species correspond to those of the selected peaks; (f) fragmenting the filtered ion species in the fragmentation cell; and (g) acquiring fragment mass spectra of the filtered ion species.

The measured signals are commonly represented by multiple data points so that the processing of the peak list reduces the amount of data points assigned to each ion species. The measured mobility-mass map of the first measurement cycle comprises a plurality of ion species and thus a plurality of peaks. Therefore, the peaks are additionally clustered in the mobility-mass space, optionally considering peaks of prior measurement cycles.

The clustering is based on assigning weights to the peaks. The more that other peaks are near to a peak to be weighted, the higher the calculated weight of that peak. In particular, the more that other peaks of high intensity are near to a peak to be weighted, the higher the calculated weight. The term "near" in this context means a distance measure $d(p1,p2)$ in the mobility-mass space. The weight assigned to a single peak can be the sum of the distance measures to all other peaks of the peak list or to a selected number of peaks which can be further weighted by the intensity of the peaks.

The minimum duration of step (d) can substantially be the duration of a single ion species after the separation in the mobility separator. The selected peaks can be included in a list used for the dynamic exclusion of peaks which have already been selected as precursors.

The method can further comprise determining peaks and preferably selected peaks (clusters) corresponding to an isotopic pattern of a substance, grouping them to an isotopic chain and selecting only a single peak of each isotopic chain in step (d). The single peak of the isotopic chain preferably corresponds to the mono-isotopic mass of the substance. Preferably, no peak of an isotopic chain is selected in step (d)

if the intensity pattern of the isotopic chain differs from a reference intensity pattern by a predetermined amount.

The weight assigned to a single peak is preferably the sum of the distance measures to all other peaks of the peak list or to a selected number of selected peaks which can be further weighted by the intensity of these peaks. The distance measure of two peaks p1 and p2 can, for example, be defined by:

$$d(p1,p2) \sim \exp(-\Delta m^2/\sigma m^2 - \Delta K^2/\sigma K^2)$$

wherein $\Delta m = m1 - m2$ is the mass difference of the two peaks p1 and p2 and $\Delta K = K1 - K2$ is the mobility difference of the two peaks p1 and p2. The method can further comprise that only a limited number of peaks of the peak list is used for calculating the weights for these peaks or for all peaks.

The substances of the substance mixture can be separated by liquid or gas chromatography or electrophoresis prior to providing them to the ion source. The mass separator can be one of a drift type mobility separator, a travelling wave separator and a trapping ion mobility separator. The mass analyzer is one of a time-of-flight mass analyzer, a time-of-flight mass analyzer with orthogonal ion injection, a RF ion trap, a DC ion trap (like an ORBITRAP®, which is an ion trap mass analyzer that consists of two outer electrodes and a central electrode, or a cassini-trap) and an ion-cyclotron-resonance trap.

BRIEF DESCRIPTION OF THE DRAWINGS

The invention can be better understood by referring to the following figures. The elements in the figures are not necessarily to scale, emphasis instead being placed upon illustrating the principles of the invention (often schematically).

DETAILED DESCRIPTION

While the invention has been shown and described with reference to a number of different embodiments thereof, it will be recognized by those skilled in the art that various changes in form and detail may be made herein without departing from the scope of the invention as defined by the appended claims.

Figure 1:
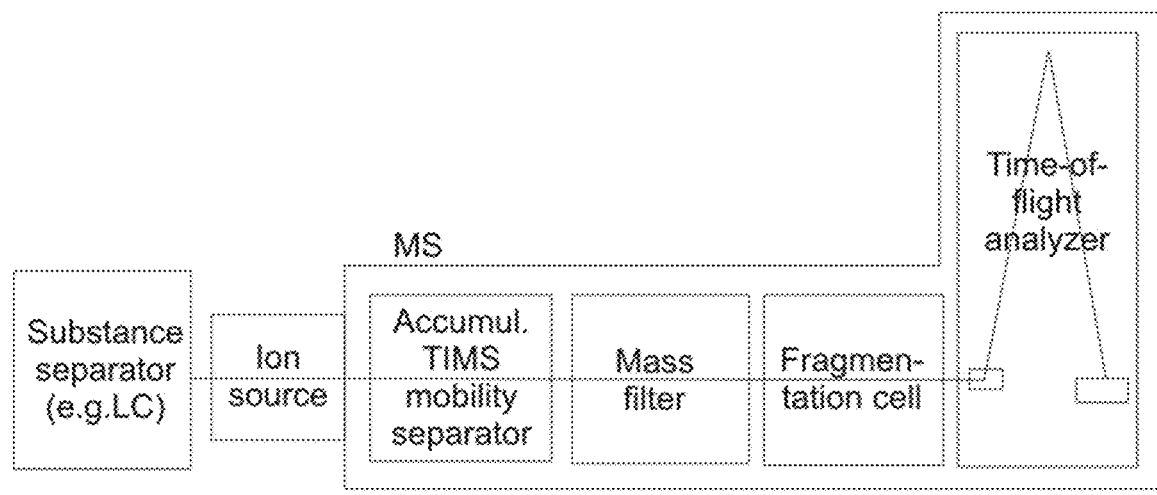
FIG. 1 shows a mass spectrometric system known from U.S. patent application Ser. No. 14/614,456 (TRAPPING ION MOBILITY SPECTROMETER WITH PARALLEL ACCUMULATION), which is incorporated herein by reference.

FIG. 1 shows a hybrid mass spectrometric system known from U.S. patent application Ser. No. 14/614,456 (TRAPPING ION MOBILITY SPECTROMETER WITH PARALLEL ACCUMULATION) which is incorporated herein by reference. The system may be used with methods according to this invention.

The instrument comprises an up-front substance separator, e.g., a liquid chromatograph (LC) which separates substances of a complex mixture in time and provides them to an ion source (e.g., an ESI source). The system further comprises a trapping ion mobility separator (TIMS) with an upstream accumulation unit, a mass filter (e.g., a quadrupole mass filter), an ion fragmentation cell, and a time-of-flight mass analyzer with orthogonal ion injection (OTOF mass analyzer).

The trapping ion mobility separator (TIMS) separates ions provided from the ion source in time according to mobility and is coupled to the downstream OTOF mass analyzer. The ions separated according to mobility are further separated in time according to mass in the OTOF mass analyzer which results in a combined mobility-mass map (MS frame) in case that the mass filter and the fragmentation cell are not in operation.

In operation, the mass filter is adjusted to select ions of a predetermined mass as precursor ions which are fragmented in the downstream fragmentation cell. The OTOF mass analyzer is then used for acquiring a fragment mass spectrum.

Figure 2:
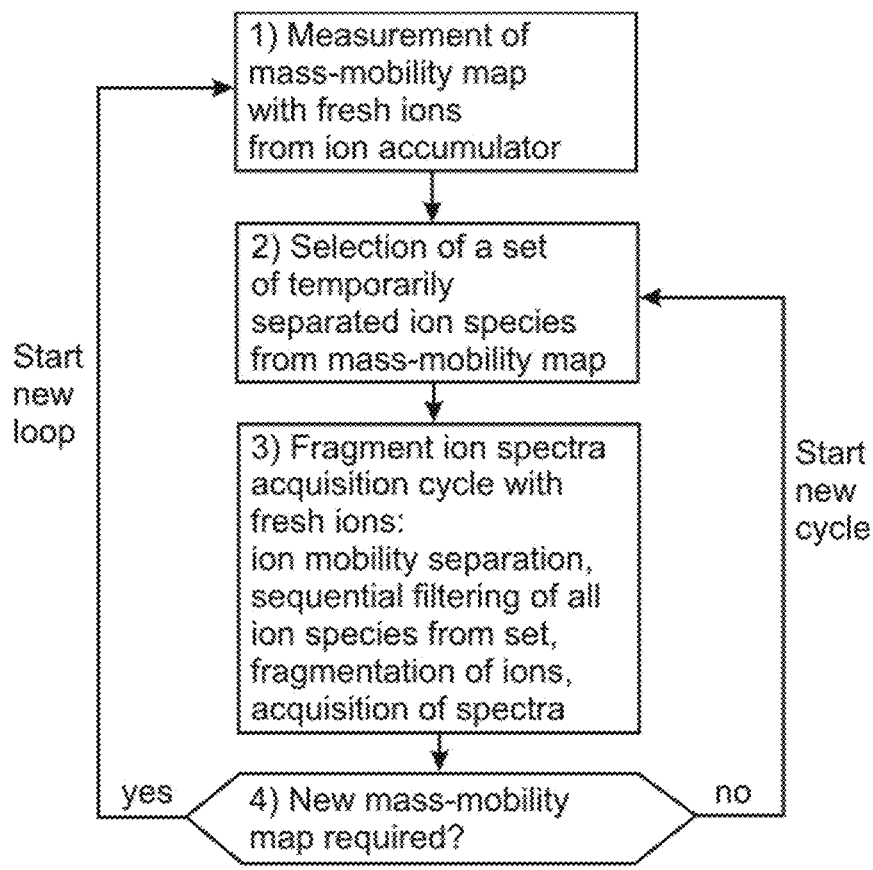
FIG. 2 shows a flowchart of a multi-cycle method for measuring fragment mass spectra known from U.S. patent application Ser. No. 14/931,163 (ACQUISITION OF FRAGMENT ION MASS SPECTRA OF IONS SEPARATED BY THEIR MOBILITY), which is incorporated herein by reference.

FIG. 2 shows a flowchart of a multi-cycle method for measuring fragment mass spectra known from U.S. patent application Ser. No. 14/931,163 (ACQUISITION OF FRAGMENT ION MASS SPECTRA OF IONS SEPARATED BY THEIR MOBILITY), which is incorporated herein by reference. The reference discloses using the mass spectrometric system of FIG. 1 for measuring a mobility-mass map and the fragment mass spectra.

In a first measurement cycle of a new loop, a mass-mobility map is measured for a first set of ions from the accumulating unit of the trapping ion mobility separator (TIMS). Ion species are selected from the mobility-mass map, e.g., in the order of intensity, from highest intensity to lower intensity. In a second measurement cycle of the same conditions as for the first measurement cycle, a second set of ions from the accumulating unit of the TIMS are again separated in time according to mobility, but the ions of interest are now selected one after the other by the mass filter, fragmented in the fragmentation cell, and the fragment ion mass spectra are acquired by the time-of-flight mass analyzer. If no new mobility-mass map is required, more ions species are selected from the same mobility-mass map, and the corresponding fragment mass spectra are acquired in a further measurement cycle. Otherwise, a new mobility-mass map is measured, starting a new loop.

Figure 3:
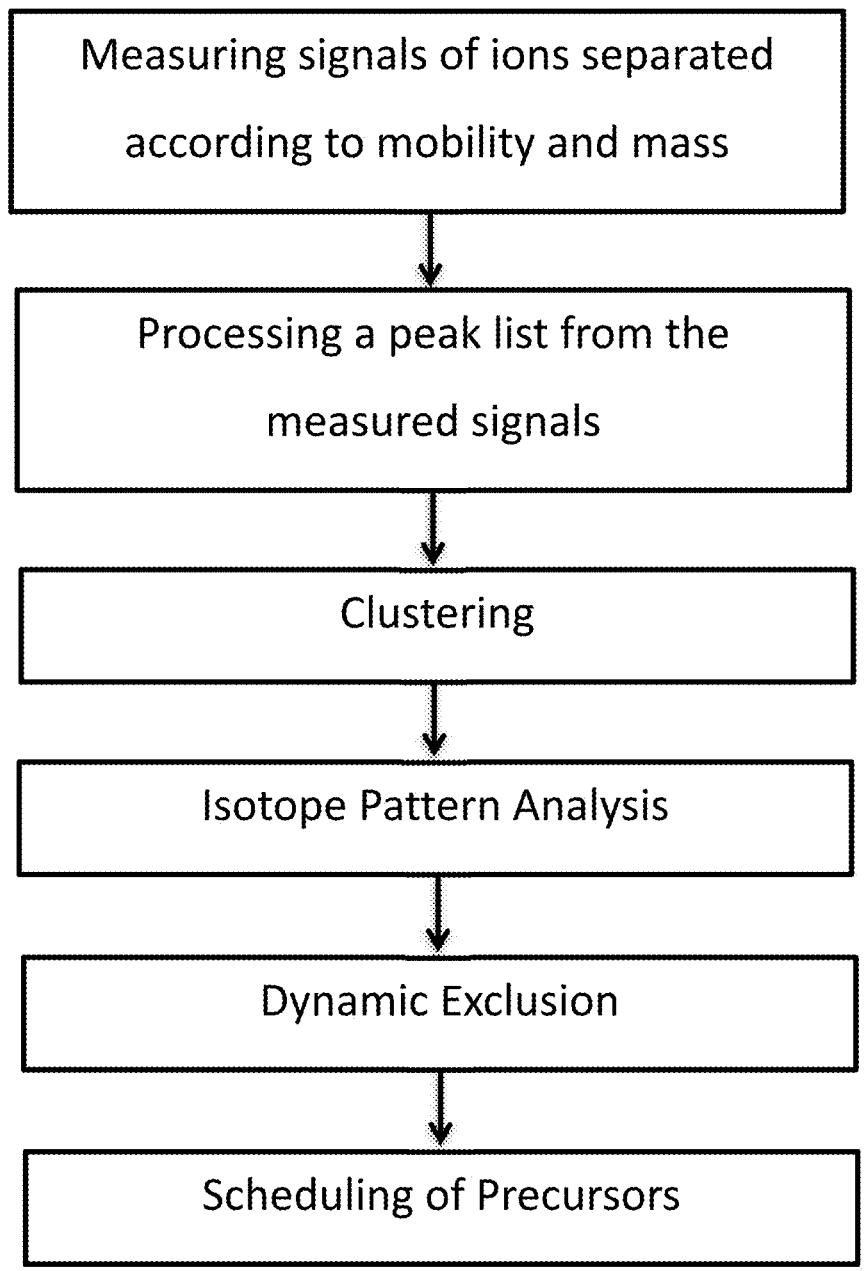
FIG. 3 shows a flowchart of method steps for precursor selection as part of a preferred embodiment of the invention.

FIG. 3 shows a flowchart of method steps for precursor selection as part of a preferred embodiment of the invention.

In a first step, ions are separated according to mobility and mass and signals of the separated ions are measured using the mass spectrometric system of FIG. 1. The ions of a single ion species which arrive at the detector of the OTOF mass analyzer produce an ion current pulse which is digitized in an analog-to-digital (A/D) converter (digitizer). The measured signal of the single ion species comprises multiple data points wherein a mobility scan time, mass and intensity are assigned to each single data point.

In a second step, a peak list is processed from the measured signals in that each single ion species is represented by a single peak to which a mobility scan time, mass and intensity is assigned. The peak picking can be performed together with the A/D conversion in an electronic circuit, e.g., a field-programmable gate array (FPGA), which is located near the A/D-converter or is integrated into the A/D-converter. The step of processing a peak list reduces the amount of data which needs to be transferred away from the A/D-converter.

In a third step, the peaks are clustered in the mobility-mass space by fast, sparse, density-based algorithms, optionally considering peaks of prior measurement cycles. The clustering is based on assigning weights to the peaks. The more that other peaks are near a peak to be weighted, the higher the calculated weight of that peak. In particular, the more that other peaks of high intensity are near a peak to be weighted, the higher the calculated weight. The term "near" in this context means a distance measure d(p1,p2) in the mobility-mass space, for example:

$$d(p1,p2) \sim \exp(-\Delta m^2/\sigma m^2 - \Delta K^2/\sigma K^2)$$

wherein $\Delta m = m1 - m2$ is the mass difference of peaks p1 and p2 and $\Delta K = K1 - K2$ is the mobility difference of the peaks p1 and p2. The weight assigned to a single peak can be the sum of the distance measures to all other peaks of the peak list or to a selected number of selected peaks wherein the distance measures can be further weighted by the intensity of the peaks.

The peaks which have weights above a predetermined threshold and/or have the highest weighted intensities within a certain neighborhood are assigned as clusters.

In a fourth step, the clusters are analyzed in terms of charge states and isotope envelopes to determine other clusters corresponding to an isotopic pattern of a substance and grouped to isotopic chains. One cluster of each isotopic chain is selected to obtain precursor candidates.

In a fifth step, some precursor candidates can be dynamically excluded depending on the history of precursors which have already been measured in preceding measurement cycles.

In a sixth step, clusters of different isotopic chains are selected for the acquisition of fragment mass spectra of a subsequent measurement cycle such that their associated mobility scan times are separated from each other by a minimum duration.

Based on the list of selected clusters, optimized measurement tasks can be generated, in particular for PASEF runs (Parallel Accumulation Serial Fragmentation). A typical PASEF schedule comprises the acquisition of more than 100 fragment mass spectra per second.

Figure 4A:
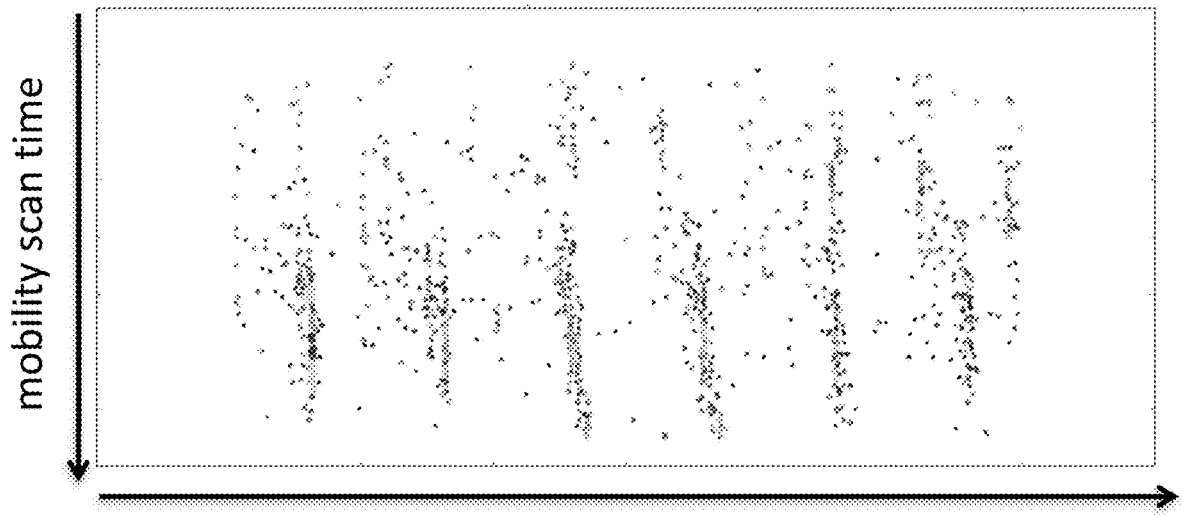
FIG. 4A shows picked peaks in a section of a mobility-mass map.
Figure 4B:
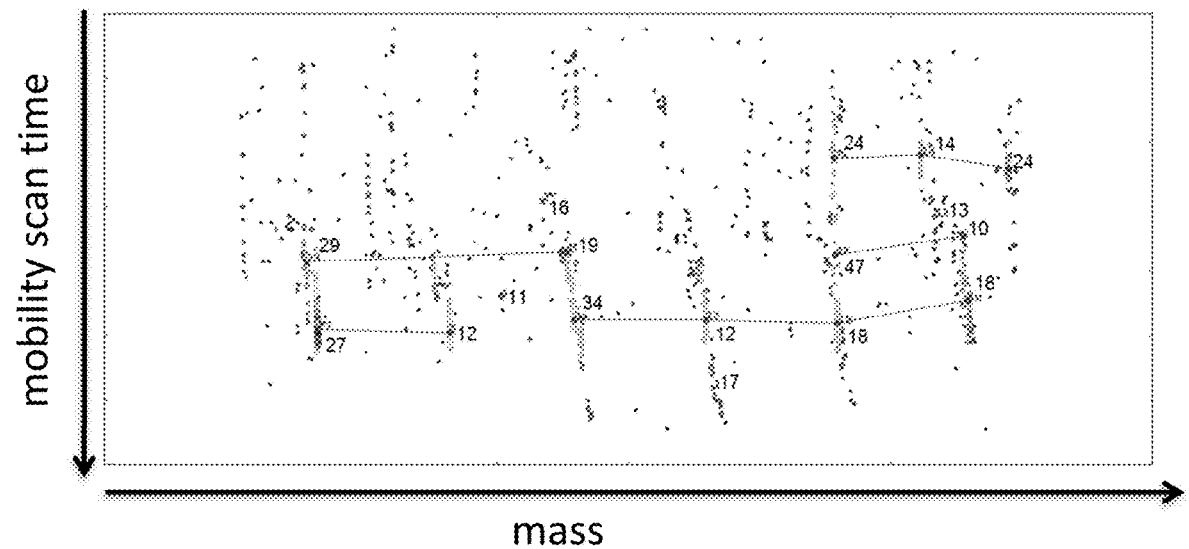
FIG. 4B shows peaks and annotated clusters in a section of a mobility-mass map wherein the clusters are grouped to isotopic chains.

FIG. 4A shows picked peaks in a section of a mobility-mass map. FIG. 4B shows peaks and annotated clusters (elected peaks of high weights) in a section of a mobility-mass map wherein the clusters are grouped to isotopic chains.

EXAMPLE

A tryptic digest of a human cancer cell line (200 ng HeLa) is separated by a nano-LC with 90 min. gradient run and analyzed on an instrument like that shown in FIG. 1, which is provided with modified acquisition software. The quality of acquired fragment mass spectra is evaluated using Mascot and PEAKS search engines. The peptide spectrum matches are normalized to a desired false discovery rate of 1%.

Figure 5:
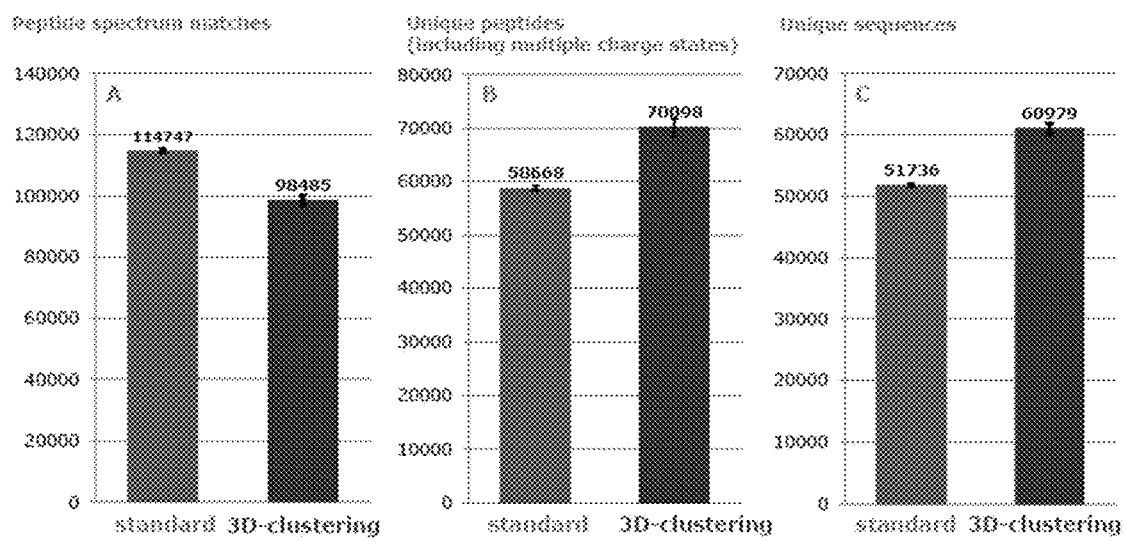
FIGS. 5 and 6 show results of a bottom-up identification run using a common precursor selection compared to the precursor selection according to the present invention.

FIG. 5 shows results of the peptide identification (Mascot, average of triplicate measurements) using a common precursor selection compared to the precursor selection according to the present invention. The common (standard) precursor selection algorithm picks signals of high intensity in the mass spectrum which result from integrating the complete mobility-mass map or slices thereof along the mobility axis.

The number of unique peptides (different charge states of the same sequence counted as peptide) and also the number of unique sequences are increased by ~15% by the precursor selection according to the invention. Due to the more accurate precursor detection and dynamic exclusion, unwanted replicate measurements are significantly reduced. Thus, the number of peptide spectrum matches is decreased by the precursor selection based on clustering in the mobility-mass space.

Figure 6:
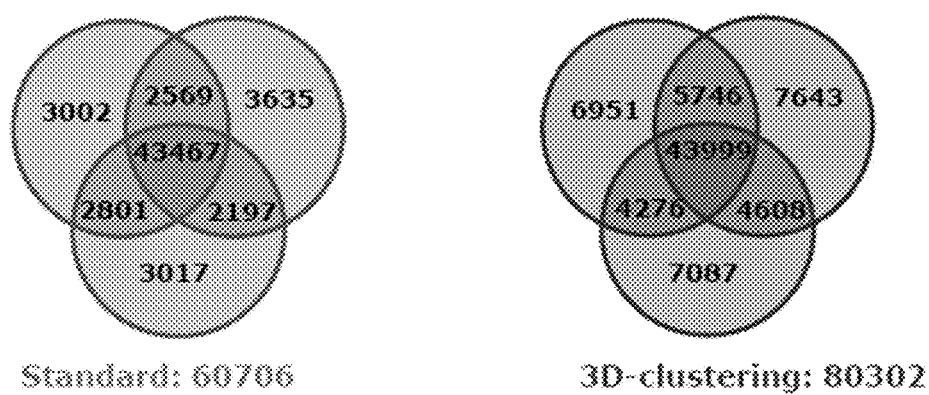
Figure 6:
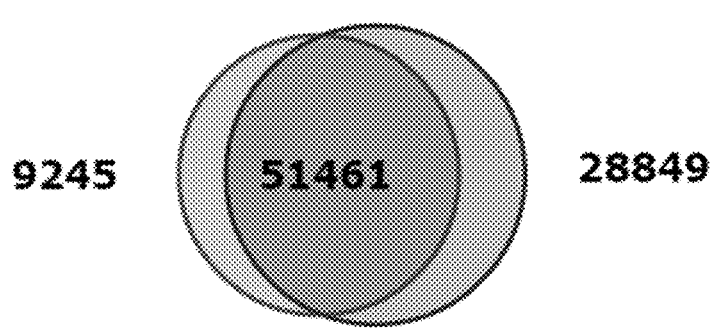

FIG. 6 shows Venn diagrams of unique sequences obtained during triplicate measurements of the common and clustering approach (top), and comparison between both algorithms (bottom).

The precursor selection according to the present invention gives an improved yield of unique peptide sequences.

The invention has been shown and described above with reference to a number of different embodiments thereof. It will be understood, however, by a person skilled in the art that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims, including any equivalent implementations, as the case may be.

The invention claimed is:

1. A method for acquiring fragment mass spectra of substances from complex substance mixtures by a mass spectrometric system comprising an ion source, an ion mobility separator, a mass filter, a fragmentation cell, and a mass analyzer, comprising the steps of a first measurement cycle:
   (a) separating a first set of ions in time according to mobility using the mobility separator and subsequently further separating the ions according to mass using the mass analyzer and measuring signals of the separated ions;
   (b) processing a peak list from the signals, wherein a mobility scan time, a mass and an intensity is assigned to each peak of the peak list;
   (c) assigning weights to the peaks wherein a higher weight is assigned to a peak when other peaks are near that peak;
   (d) selecting peaks which have weights above a predetermined threshold and/or have the highest weighted intensities within a certain neighborhood and whose mobility scan times are separated from each other by a minimum duration;

and further comprising the steps of a second measurement cycle:
   (e) separating a second set of ions in time according to mobility using the mobility separator and subsequently filtering ion species according to mass using the mass filter wherein the mobility scan times and the masses of the filtered ion species correspond to those of the selected peaks;
   (f) fragmenting the filtered ion species in the fragmentation cell; and
   (g) acquiring fragment mass spectra of the filtered ion species.

2. The method according to claim 1, further comprising determining peaks corresponding to an isotopic pattern of a substance, grouping them to an isotopic chain and selecting only a single peak of each isotopic chain in step (d).

3. The method according to claim 2, further comprising determining selected peaks which correspond to an isotopic pattern of a substance, grouping them to an isotopic chain and selecting only a single peak of each isotopic chain in step (d).

4. The method according to claim 3, wherein the single peak of the isotopic chain corresponds to the mono-isotopic mass of the substance.

5. The method according to claim 2, wherein no peak of an isotopic chain is selected in step (d) if the intensity pattern of the isotopic chain differs from a reference intensity pattern by a predetermined amount.

6. The method according to claim 1, wherein weight assigned to a single peak is the sum of the distances measured to all other peaks of the peak list or to a selected number of selected peaks which can be further weighted by the intensity of these peaks.

7. The method according to claim 6, wherein the distance measure d between two peaks p1 and p2 is $d(p1,p2) \sim \exp(-\Delta m^2/\sigma m^2 - \Delta K^2/\sigma K^2)$ wherein $\Delta m = m1 - m2$ is the mass difference of peaks p1 and p2 and $\Delta K = K1 - K2$ is the mobility difference of the peaks p1 and p2, wherein m1 and K1 correspond to peak p1 and m2 and K2 correspond to peak p2, and wherein $\sigma m$ and $\sigma K$ are parameters of the distance measure d.

8. The method according to claim 1, wherein the substances of the substance mixture are separated by liquid or gas chromatography or electrophoresis prior to providing them to the ion source.

9. The method according to claim 1, wherein the mobility separator is one of a drift type mobility separator, a travelling wave separator and a trapping ion mobility separator.

10. The method according to claim 1, wherein the mass analyzer is one of a time-of-flight mass analyzer, a time-of-flight mass analyzer with orthogonal ion injection, a RF ion trap, a DC ion trap and an ion-cyclotron-resonance trap.

11. The method according to claim 1, wherein the minimum duration is substantially the duration of a single mobility species after the separation in the mobility separator.

12. The method according to claim 1, wherein a limited number of peaks of the peak list is used for calculating the weights for these peaks or for all peaks.

13. The method according to claim 1, wherein the selected peaks are included in a list used for the dynamic exclusion of peaks which have already been used to select precursors.

14. The method according to claim 1, wherein, in step (a), the ions are separated in time according to mass in a time-of-flight analyzer and ions of each single ion species having a given mobility and mass generate a pulsed ion current at the ion detector which is digitized in an A/D-converter such that the measured signal of the single ion species comprises multiple data points and each one of the data points is assigned to a mobility scan time, mass and intensity.

15. The method according to claim 14, wherein the processing of the peak list is performed together with the digitizing in an electronic circuit which operates together with the A/D-converter.

16. The method according to claim 15, wherein the steps (b) to (c) are performed in less than one second.

17. The method according to claim 14, wherein the steps (b) to (c) are performed in less than one second.

18. The method according to claim 14, wherein the steps (b) to (c) are performed in less than 300 ms.

19. The method according to claim 14, wherein the steps (b) to (c) are performed in less than 100 ms.

20. The method according to claim 15, wherein the steps (b) to (c) are performed in less than 300 ms.

21. The method according to claim 15, wherein the steps (b) to (c) are performed in less than 100 ms.

22. The method according to claim 1 wherein, in step (c), the more that other peaks of high intensity are near to a peak to be weighted, the higher the calculated weight.

* * * * *